(12) United States Patent
Hung et al.

(10) Patent No.: US 8,643,833 B1
(45) Date of Patent: Feb. 4, 2014

(54) SYSTEM FOR INSPECTING SURFACE DEFECTS OF A SPECIMEN AND A METHOD THEREOF

(75) Inventors: Min-Wei Hung, Hsinchu (TW); Hsin-Yi Tsai, Hsinchu (TW); Kuo-Cheng Huang, Hsinchu (TW); Chun-Yao Huang, New Taipei (TW)

(73) Assignees: National Applied Research Laboratories, Taipei (TW); MFC Sealing Technology Co., Ltd., New Taipei (TW)

( * ) Notice: Subject to any disclaimer, the term of this patent is extended or adjusted under 35 U.S.C. 154(b) by 0 days.

(21) Appl. No.: 13/600,726

(22) Filed: Aug. 31, 2012

(51) Int. Cl.
*G01N 21/00* (2006.01)
(52) U.S. Cl.
USPC ................... 356/237.2; 356/237.1
(58) Field of Classification Search
USPC .......................................... 356/237.1–237.5
See application file for complete search history.

(56) References Cited

U.S. PATENT DOCUMENTS

| | | | | |
|---|---|---|---|---|
| 6,630,996 B2 * | 10/2003 | Rao et al. | | 356/237.5 |
| 6,740,896 B2 * | 5/2004 | Nagamura | | 250/559.45 |
| 6,861,268 B2 * | 3/2005 | Iwabuchi | | 438/14 |
| 7,714,997 B2 * | 5/2010 | Shibata et al. | | 356/237.2 |
| 7,869,024 B2 * | 1/2011 | Urano et al. | | 356/237.2 |
| 2001/0013935 A1 * | 8/2001 | Watanabe et al. | | 356/600 |
| 2004/0169851 A1 * | 9/2004 | Yang et al. | | 356/237.2 |
| 2004/0263835 A1 * | 12/2004 | Miyakawa et al. | | 356/237.2 |
| 2008/0225298 A1 * | 9/2008 | Fairley et al. | | 356/445 |
| 2008/0239292 A1 * | 10/2008 | Kawaki et al. | | 356/73 |
| 2009/0257647 A1 * | 10/2009 | Yoshitake et al. | | 382/149 |

* cited by examiner

*Primary Examiner* — Sang Nguyen
(74) *Attorney, Agent, or Firm* — Muncy, Geissler, Olds & Lowe, PLLC

(57) ABSTRACT

An inspection system and method for inspecting the surface defects of the specimen is provided. The inspection system includes a laser focus module, a microscope objective module, an image pick-up module, and a process module. The laser focus module configured to emit laser beam on the specimen by a predetermined angle relative to a surface of the specimen, and to generate scattered light and reflected light when the laser beam irradiates on the surface defects of the specimen. The process module can calculate the real size of the defects by using the intensity information obtained from the image pick-up module and the microscope objective module or using the diameter information obtained from the reflected light image while the reflected light projects on a screen.

16 Claims, 10 Drawing Sheets

SYSTEM FOR INSPECTING SURFACE DEFECTS OF A SPECIMEN AND A METHOD THEREOF

BACKGROUND OF THE INVENTION

1. Field of the Invention

The present invention generally relates to a system for inspecting surface defects of a specimen and a method thereof, in particular to a system and a method for inspecting the surface defects of the wafer by using the scattered light.

2. Description of the Related Art

In field of semiconductor industry, it is important for the silicon substrate surface to be clean because the defects attached on the surface of the wafer will have great influence upon the chip manufacture process, such as the short circuit phenomenon. Therefore, inspecting the defects of the wafer surface becomes a significant issue in the chip manufacture process for increasing the yield rate and decreasing the cost of manufacturing process.

The wafer inspection systems which are used to detect surface defects on the silicon wafer can be divided into two types, the bright field (BF) system and the dark field (DF) system. In the BF system, the images of surface feature on wafer are obtained directly by using a camera and a microscope object lens, and the particle sizes can be measured rapidly and directly. In general, in order to acquire the image of micro-level particles, the higher magnification object lens, higher resolution image sensor, and shorter-wavelength light are required. Hence the cost of BF system will increase with the amount of its accessories, and its inspection speed becomes very slow due to the smaller inspection area. Since the DF system is able to collect the scattered light from the wafer surface, the size and number of particles can be evaluated from the intensity of scattered light. However, the DF system cannot get the real size of particles on the wafer surface, so it only can be applied to the inspection of bare wafer.

SUMMARY OF THE INVENTION

Therefore, it is a primary objective of the present invention to provide an inspection system for inspecting the surface defects of the specimen and an inspection method thereof to achieve the effect of reducing the inspection cost, increasing the inspection speed and calculating the real size of each defect on a specimen surface.

To achieve the foregoing objective, the present invention provides an inspecting system for inspecting surface defects of a specimen, the system comprising a laser focus module, a microscope objective module, an image pick-up module, and a process module. The laser focus module configured to emit laser beam on the specimen by a predetermined angle relative to a surface of the specimen, and to generate scattered light when the laser beam irradiates on the surface defects of the specimen. The microscope objective module configured in a scattering area of the scattered light to receive the scattered light. The image pick-up module includes a charge-coupled device connected to the microscope objective module and arranged for transforming the scattered light into a digital signal, and the process module coupled to the charge-coupled device and arranged for calculating sizes of the surface defects by analyzing the digital signal.

Preferably, the predetermined angle may range from approximately 15° to approximately 40°.

Preferably, the predetermined angle may range from approximately 20° to approximately 30°.

Preferably, the process module may calculate size of each of the surface defects by analyzing intensity of the scattered light according to the digital signal.

Preferably, the inspection system may further include a reflected light capture module to capture a reflected light image, and the process module may selectively calculate the size of each of the surface defects by analyzing diameters of caustic curves from the reflected light image.

Preferably, the laser focus module may include a laser source, a beam expander and a focusing lens set, and the beam expander is configured between the laser source and the focusing lens set.

Preferably, the laser beam may be the green light laser.

Preferably, the inspection system may further include a platform holding up the specimen to revolve and cause the specimen to rotate correspondingly, and the laser beam accordingly irradiates on the surface of the specimen in a circular way.

Preferably, the inspection system may further include a driving module which is connected to the laser focus module and the image pick-up module to drive the laser focus module and the image pick-up module to move simultaneously, and to cause the laser beam to irradiate on the surface of the specimen in a straight way.

To achieve the foregoing objective, the present invention further provides an inspection method for inspecting surface defects of a specimen, the method includes: using a laser focus module to emit laser beam on the specimen by a predetermined angle relative to a surface of the specimen, and to generate scattered light when the laser beam irradiates on the surface defects of the specimen; using a microscope objective module configured in a scattering area of the scattered light to receive the scattered light; using an image pick-up module connected to the microscope objective module, wherein the image pick-up module includes a charge-coupled device arranged for transforming the scattered light into a digital signal; and using a process module coupled to the charge-coupled device to arrange for obtaining sizes of the surface defects by analyzing the digital signal.

Preferably, the predetermined angle may range from approximately 15° to approximately 40°.

Preferably, the predetermined angle may range from approximately 20° to approximately 30°.

Preferably, the step of using a process module may further include using the process module to analyze intensity of the scattered light according to the digital signal to calculate the size of each of the surface defects.

Preferably, the inspection method may further include using a reflected light capture module to capture a reflected light image, and using the process module to calculate the size of each of the surface defects by analyzing diameters of caustic curves from the reflected light image.

Preferably, the laser focus module may include a laser source, a beam expander and a focusing lens set, and the beam expander is configured between the laser source and the focusing lens set.

Preferably, wherein the laser beam may be a green light laser.

Preferably, the inspection method may further include using a platform to hold up the specimen, wherein the platform revolves and then causes the specimen to rotate correspondingly, and the laser beam accordingly irradiates on the surface of the specimen in a circular way.

Preferably, the step of using a platform may further include using a drive module connected to the laser module and the image pick-up module to drive the laser module and the image pick-up module to move simultaneously, and causes the laser beam to irradiate on the surface of the specimen in a straight way.

The inspection system and method for inspecting the surface defects of a specimen according to the present invention can calculate the real size of each defect on the surface of the specimen by analyzing the intensity of the scattered light or the diameter of the caustic curves captured by the reflected light capture module, so that the present invention has the following advantages.

Since the inspection system and method of the present invention do not need a high magnification object lens and a high resolution image sensor for acquiring the image of micro-level defects or particles, the present invention can increase the inspection speed because of the larger inspection zone and decrease the cost because the present invention only need to get the diameter of the caustic curves from the reflected light image or the intensity of the scattered light to calculate the size of each defect by using the process module.

BRIEF DESCRIPTION OF THE DRAWINGS

The detailed structure, operating principle and effects of the present invention will now be described in more details hereinafter with reference to the accompanying drawings that show various embodiments of the invention as follows.

DETAILED DESCRIPTION OF THE PREFERRED EMBODIMENTS

The technical content of the present invention will become apparent by the detailed description of the following embodiments and the illustration of related drawings as follows.

Figure 1:
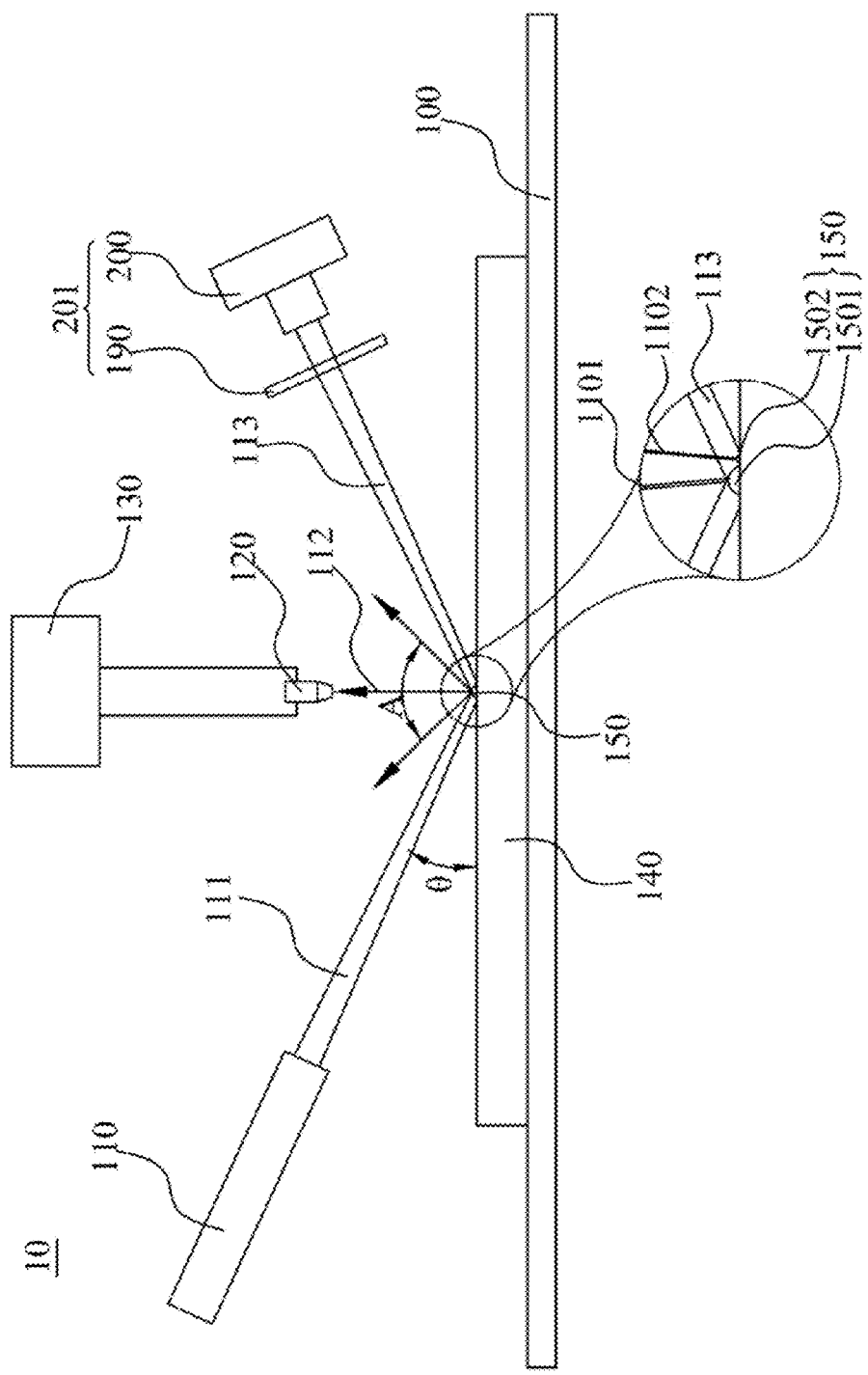
FIG. 1 is a first schematic view of an embodiment of an inspection system according to the present invention.

With reference to FIG. 1 for a schematic view of an embodiment of an inspection system according to the present invention, the inspection system 10 is applied to inspect the surface defects of a specimen. The inspect system 10 includes a platform 100, a laser focus module 110, a microscope objective module 120, an image pick-up module 130, reflected light capture module 201 and a process module 180 (shown in FIG. 2), wherein the platform 100 is used to hold up the specimen.

The specimen of the present embodiment is a silicon wafer 140, but is not limited thereto. In other embodiments of the present invention, the specimen can be a workpiece or an article and the inspection system 10 of the present invention can detect particles, motes, roughness and the like on a surface of the workpiece or the article.

The laser focus module 110 is configured to emit the laser beam 111 on the silicon wafer 140 by a predetermined angle θ relative to a surface of the silicon wafer 140, and when the laser beam 111 irradiates on the surface defects 150 of the silicon wafer 140, the laser beam 111 will reflect and partially scatter to cause reflected light 113 and scattered light 112 due to the irregular surface formed by the defects 150.

More specifically, the laser focus module 110 is configured to emit the laser beam 111 on the silicon wafer 140 by a predetermined angle θ relative to the surface of the silicon wafer 140, wherein while the image pick-up module 130 and the microscope objective module 120 are disposed right above the point on which the laser beam 111 irradiates, the predetermined angle θ ranges from approximately 15° to approximately 40°. More preferably, the predetermined angle ranges from approximately 20° to approximately 30°, but is not limited thereto. When the image pick-up module 130 and the microscope objective module 120 are disposed near right above the point on which the laser beam 111 irradiates, the predetermined angle θ can thus adjust outside the range of 15° to 40° to make the image pick-up module 130 and the microscope objective 120 be able to receive the better scattered light for observing and analyzing.

Figure 2:
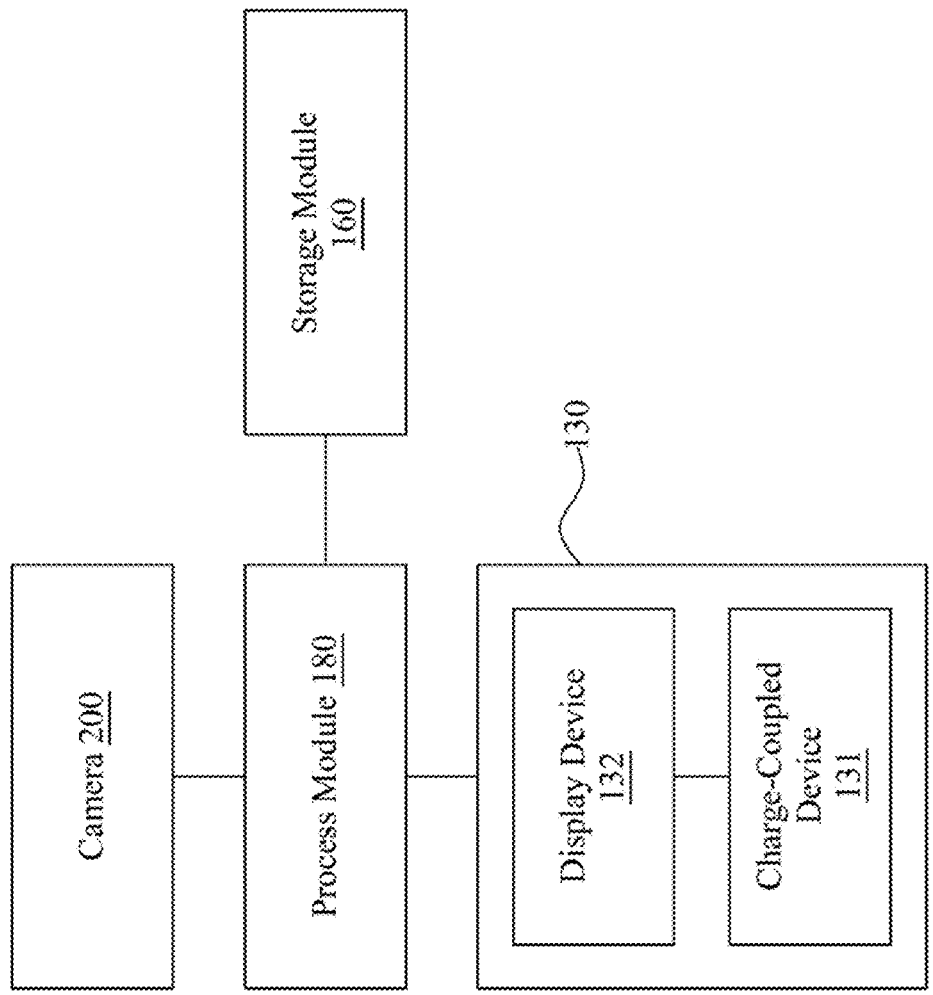
FIG. 2 is the signal analyzing block diagram of an embodiment of the process module according to the present invention.

With further reference FIG. 2, which is the signal analyzing block diagram of the process module 180. The microscope objective 120 is configured in a scattering area A of the scattered light 112 to receive the scattered light 112. The image pick-up module 130 includes a charge-coupled device (CCD) 131 which is connected to the microscope objective 120 and is arranged for transforming the scattered light 112 into a digital signal. The process module 180 is coupled to the charge-coupled device 131 and is arranged for calculating sizes of the surface defects 150 by analyzing the digital signal.

The image pick-up module 130 further includes a display device 132 and a storage device 160. The display device 132 is coupled to the charge-coupled device 131 for displaying the scattered light image by receiving the digital image signal from the charge-coupled device 131 and the storage module 160 is coupled to the process module 180 for storing the distribution information of the surface defects 150 of the silicon wafer 140.

The microscope objective 120 can receive the scattered light 112 and guides the scattered light 112 to the image pick-up module 130, a detector worker can observe phenomenon or the condition of the scattered light 112 by using the microscope objective 120.

In the present embodiment, the process module 180 calculates the size of each surface defect 150 by analyzing the intensity of the scattered light 112 according to the digital signal transformed by the charge-coupled device 131 when receiving the scattered light 112, but is not limited thereto. In the other embodiments of the present invention, the process module 180 can couple to the camera 200, so as to calculate the size of each surface defect 150 by analyzing diameters of caustic curves from the reflected light image.

Figure 3A:
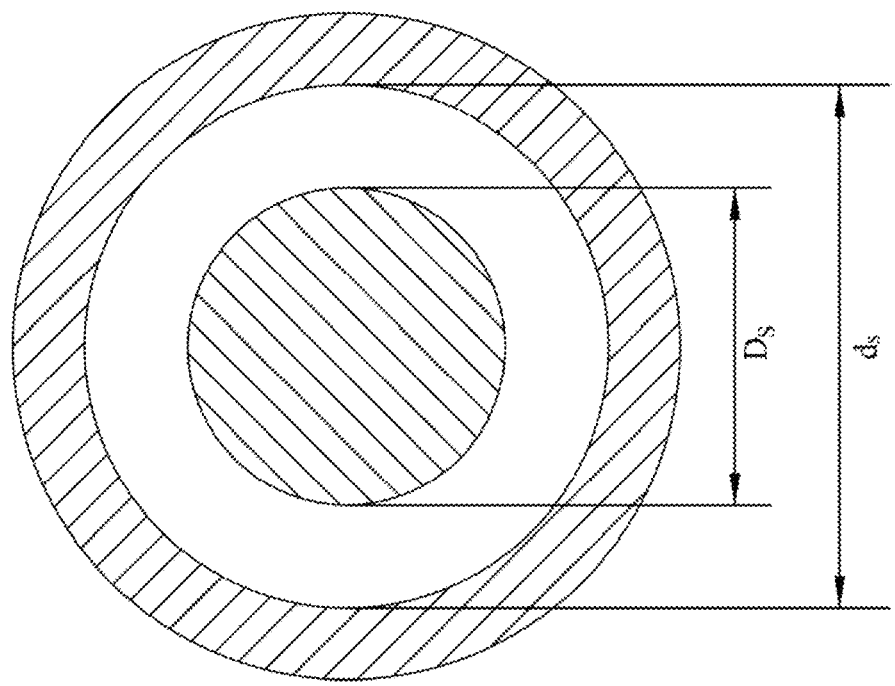
FIG. 3A and FIG. 3B are the schematic view of the diameters of the caustic curves from the reflected light image.
Figure 3B:
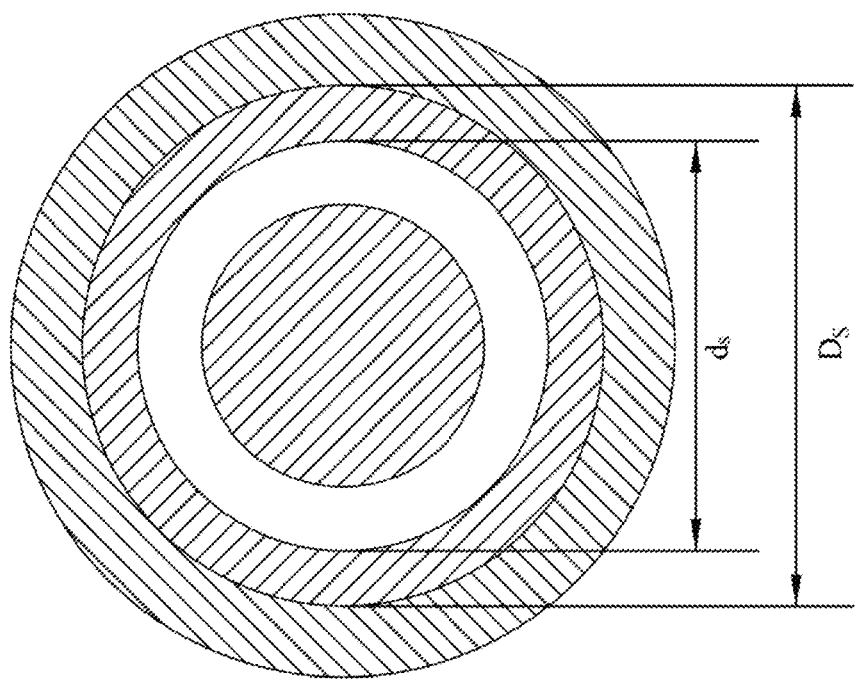

In other words, when the reflected light capture module 201 captures the reflected light image by using the screen 190 and the camera 200 shown in FIG. 1, the process module 180 can analyze the diameters of the caustic curves from the reflected light image as shown in FIGS. 3A and 3B. More specifically, in optics, a caustic is the envelope of light rays reflected or refracted by a curved surface or object, or the projection of that envelope of rays on another surface. The caustic is a curve or surface to which each of the light rays is tangent, defining a boundary of an envelope of rays as a curve of concentrated light. Therefore, in some embodiments of the present invention can obtain the diameter of the caustic curves by using the reflected light projected on the screen 190. During the inspection operation, the reflected light 113 and caustics of defects 150 will be observed on the screen 190 simultaneously. In FIG. 3A, the diameter of caustics $d_S$ is larger than the reflected laser spot (reflected light 113) $D_S$ because the size of the defect 150 is smaller than the wavelength of the laser beam 111 according to Rayleigh scattering theory. And in FIG. 3B, the diameter of the caustics $d_S$ is smaller than the reflected laser spot (reflected light 113) $D_S$ because the size of the defect 150 is larger than the wavelength of the laser beam 111 according to the Mie scattering theory.

For more complete understanding, the method of the process module 180 calculating the real size of each surface defects 150 will be described herein.

When the laser beam 111 irradiates on the silicon wafer 140, the laser beam 111 will be reflected from the silicon wafer 140 in most cases, but the optical path of the reflected beam will be changed due to the surface defects, such as the particles and the roughness of the silicon wafer surface. Since when performing the particle inspection, the intensity of scattered light caused by defects will be obtained by the charge-coupled device and the diameter of the caustic curves will be observed on the screen 190, and there is a relationship between the real particle size ($d_P$), the diameter of reflected caustics ($d_S$) and the reflected light intensity of caustics ($I_P$) which can be written as follows:

$$d_{P1} = \alpha_1 d_s + \beta_1$$

$$d_{P2} = \alpha_2 I_P + \beta_2$$

where $\alpha_1, \beta_1$ and $\alpha_2, \beta_2$ are the shape and intensity factors of particle, which depend on the sharpness and contrast of caustic or scattered light.

If the real particle size $d_{P1}$ and $d_{P2}$ are measured by scanning electron microscope and optical microscope in advance, and from the screen 190, the diameter of two particle caustics diameter $d_{S1}$, and $d_{S2}$ can be obtained and the intensity of scattered light $I_{P1}$, and $I_{P2}$ can be analyzed from the charge-coupled device, then the shape factors ($\alpha_1, \beta_1$) and intensity factors ($\alpha_2, \beta_2$) can be formulated as follows:

$$\begin{bmatrix} \alpha_1 \\ \beta_1 \end{bmatrix} = \begin{bmatrix} \dfrac{1}{d_{S1} - d_{S2}} & \dfrac{-1}{d_{S1} - d_{S2}} \\ \dfrac{-d_{S2}}{d_{S1} - d_{S2}} & \dfrac{d_{S1}}{d_{S1} - d_{S2}} \end{bmatrix} \begin{bmatrix} d_{P1} \\ d_{P2} \end{bmatrix}$$

$$\begin{bmatrix} \alpha_2 \\ \beta_2 \end{bmatrix} = \begin{bmatrix} \dfrac{1}{I_{P1} - I_{P2}} & \dfrac{-1}{I_{P1} - I_{P2}} \\ \dfrac{-I_{P2}}{I_{P1} - I_{P2}} & \dfrac{I_{P1}}{I_{P1} - I_{P2}} \end{bmatrix} \begin{bmatrix} d_{P1} \\ d_{P2} \end{bmatrix}$$

From the formulae described above, the defects, such as particles and roughness, on the silicon wafer surface can be detected easily by the present invention. Referring to the exploding part of FIG. 1, when the laser beam 111 irradiates on the defects 1501 and 1502, wherein the defect 1501 causes the scattered light 1101, and the defect 1502 causes the scattered light 1102, the process module 180 can exactly calculate the real size of defects 1501 and 1502 respectively by analyzing the intensity of the scattered light 1101 and 1102 or obtaining the diameter of the caustic curve from the reflected light image projected on the screen 190. Therefore, compare to the prior art, the present invention can offer a more rapid way to evaluate the defects on the surface of the silicon wafer because the present invention has a larger inspection area.

Furthermore, the present invention can decrease the cost of the defects inspection process because the present invention does not need a high resolution image sensor or a high magnification object lens, and the present invention only need to obtain the diameter of the caustic curve from the reflected light image or the intensity information from the digital signal transformed by the charge-coupled device. In addition, through the present invention, the sizes of each defect can be calculated by the process module 180 and unlike the bright field system which needs expensive element or unlike the dark field system which can only detect the bare wafer since the dark field system can not get the real size of defects on the silicon wafer surface.

Figure 4:
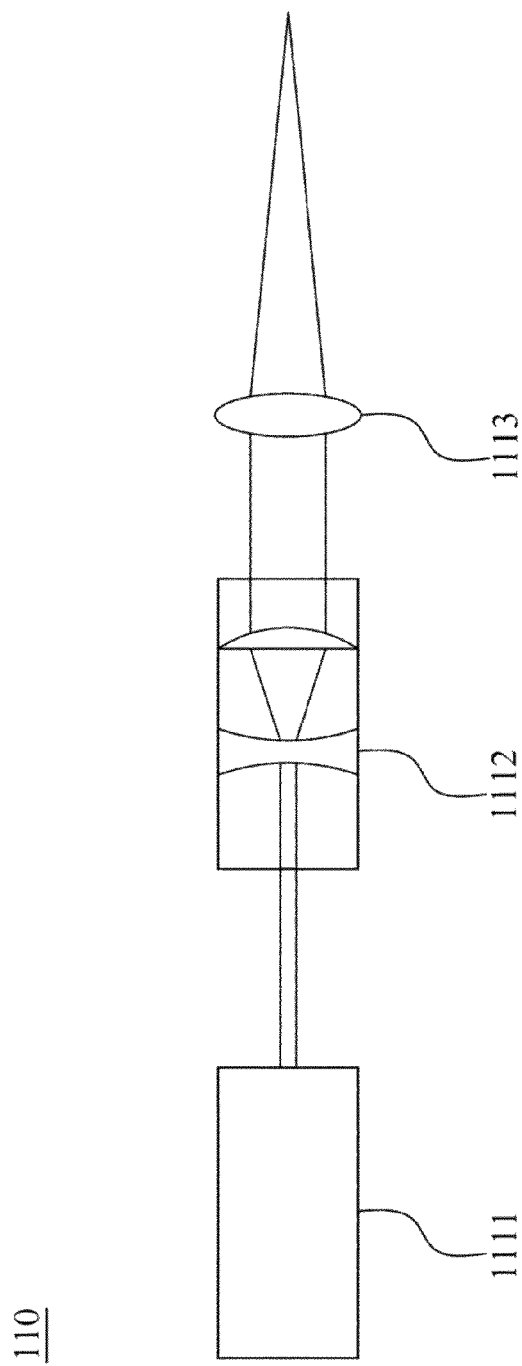
FIG. 4 is the schematic view of an embodiment of the laser focus module according to the present invention.

With reference to FIG. 4, the laser focus module 110 can include a laser source 1111, a beam expander 1112 and a focusing lens set 1113, and the beam expander 1112 is configured between the laser source 1111 and the focusing lens set 1113 for expanding the diameter of the laser beam. The focusing lens set 1113 is used to focus laser beam 111 to incident on the silicon wafer 140. In this focus module 110, the focused laser spot size $d_L$ can be calculated from the following equation:

$$d_L = \frac{4fM^2\lambda}{\pi D} + \frac{kD^3}{f^2}$$

where D is the diameter of original laser beam, f is the focal length of focusing lens, $\lambda$, is the wavelength of laser light, $M^2$ is the beam quality factor, and k is the refractive index factor. Generally, the second term of the focused laser spot size formula can be neglected if the diameter of original laser beam is less than 20 mm. Consequently, the smaller laser spot size can be obtained if the diameter of original laser beam increases. In the present embodiment, the laser beam 111 is a green light laser, but is not limited thereto. In the other embodiments of the present invention, the laser beam 111 can be the red light laser or other type of lasers.

For more complete understanding to the present embodiment, the real example and test result will be introduced herein. In this example, a 532 nm-5 mW laser is used to focus on the surface of silicon wafer and generate the scattered light and reflected light. The diameter of original laser beam is 1 mm, the beam quality factor $M^2$ is about 2, and the focal length of focusing lens is 120 mm. According to the focused laser spot size formula, the laser spot size can be reduced to 20 um using an 8× beam expander. In order to calculate the factors $\alpha$ and $\beta$, this example measures the real size of the defects on silicon wafer with the use of SEM. The dimension of sample is 15×15 $mm^2$, and an 8 nm thin film of platinum (Pt) is deposited on the sample to cover the micro or submicron defects and to prevent them disappeared. Moreover, this example uses the optical microscope (OM) and a 20× objective lens to verify if the laser spot can cover the particles which are measured by SEM.

Figure 5:
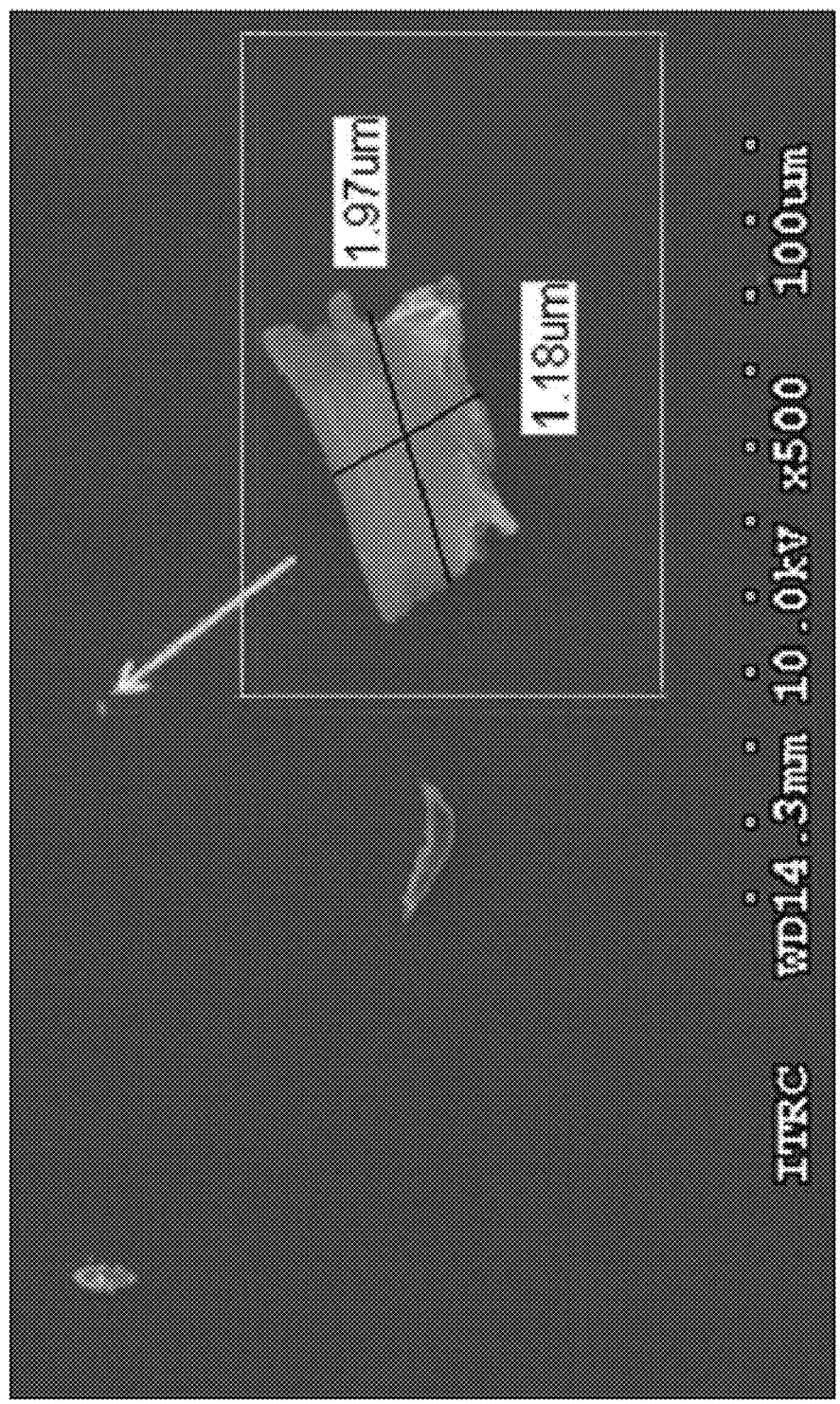
FIG. 5 is the target area having the defects in the example by SEM.
Figure 6:
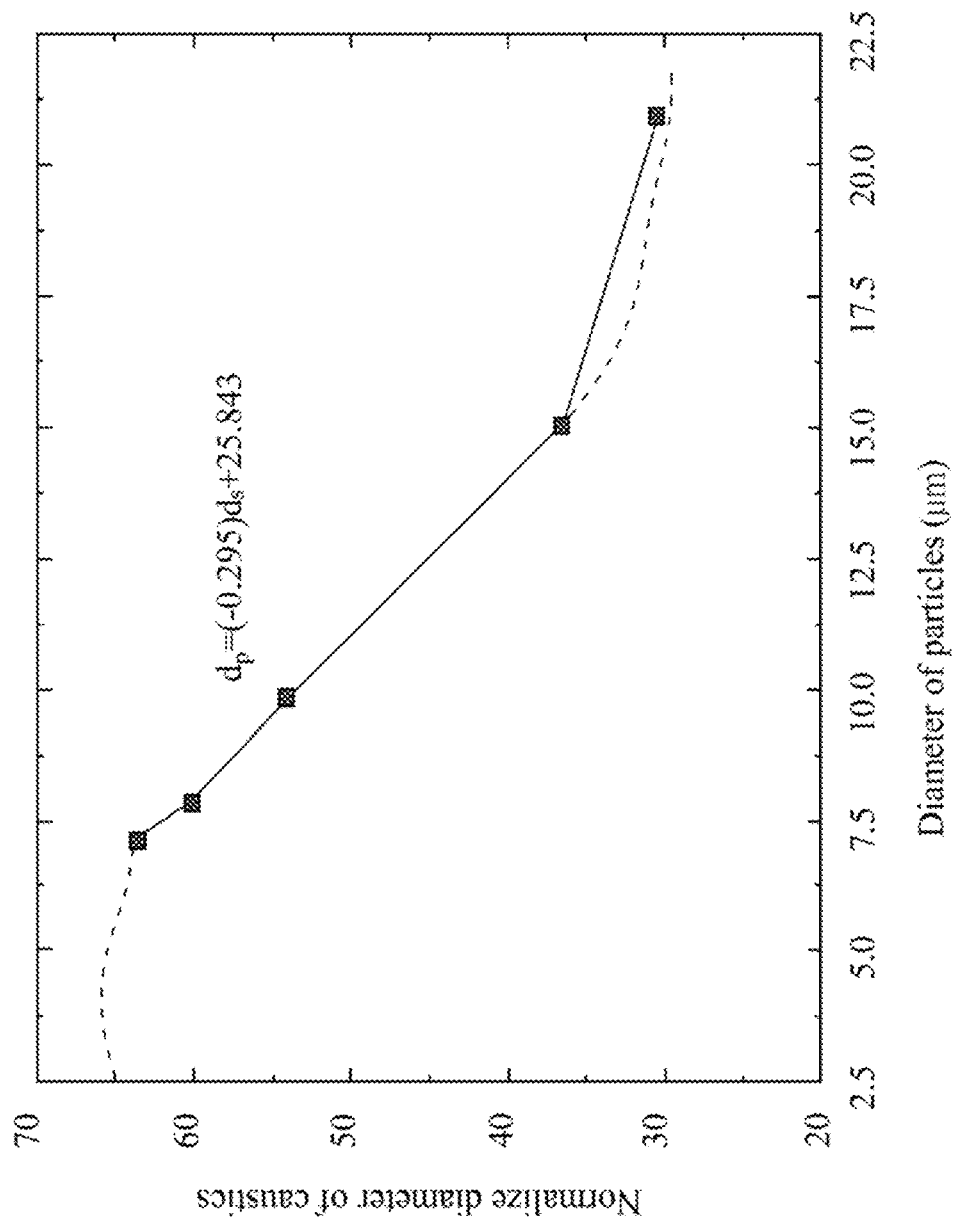
FIG. 6 is a diagram of the relationship between the diameter of the caustics and the defects sizes.
Figure 7:
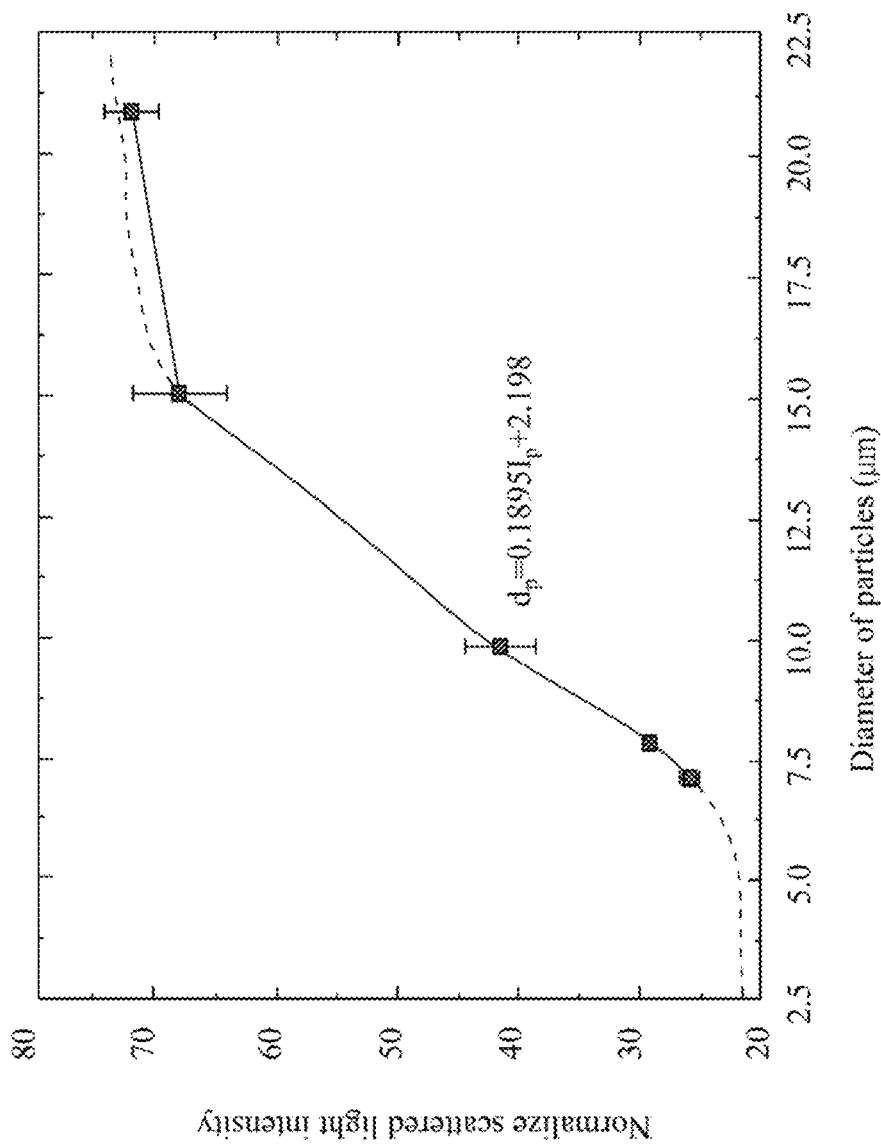
FIG. 7 is a diagram of the relationship between the intensity of scattered light and defects sizes.

FIG. 5 shows the target area in the example by SEM, and the dimension of target particle is 1.97×1.18 $um^2$. In the following example, the dimension of target particle in SEM image can be measured, which can be a good reference to calculate the sizes of other particles observed by OM. In the example, the reflected laser spot Ds is about 34 mm. There are four particles of different sizes are chosen to calibrate the diameter and intensity of caustics. From the FIG. 6, this example found that the diameter of caustics decreases with the increase of the defect size. The reason is that the larger defect causes the more obvious reflected wavefront and produces the smaller caustics. In addition, the larger particle will induce higher intensity of scattered light, shown in FIG. 7. Furthermore, the diameter of caustic curves and the intensity of scattered light could not keep the linear relations to particle size when the particle size is more than 15 um and less than 5 um. In fact, if the particle size is less than 5 um, the reflected wavefront will be too closed to the diffraction wavefront to evaluate the particle size.

Figure 8:
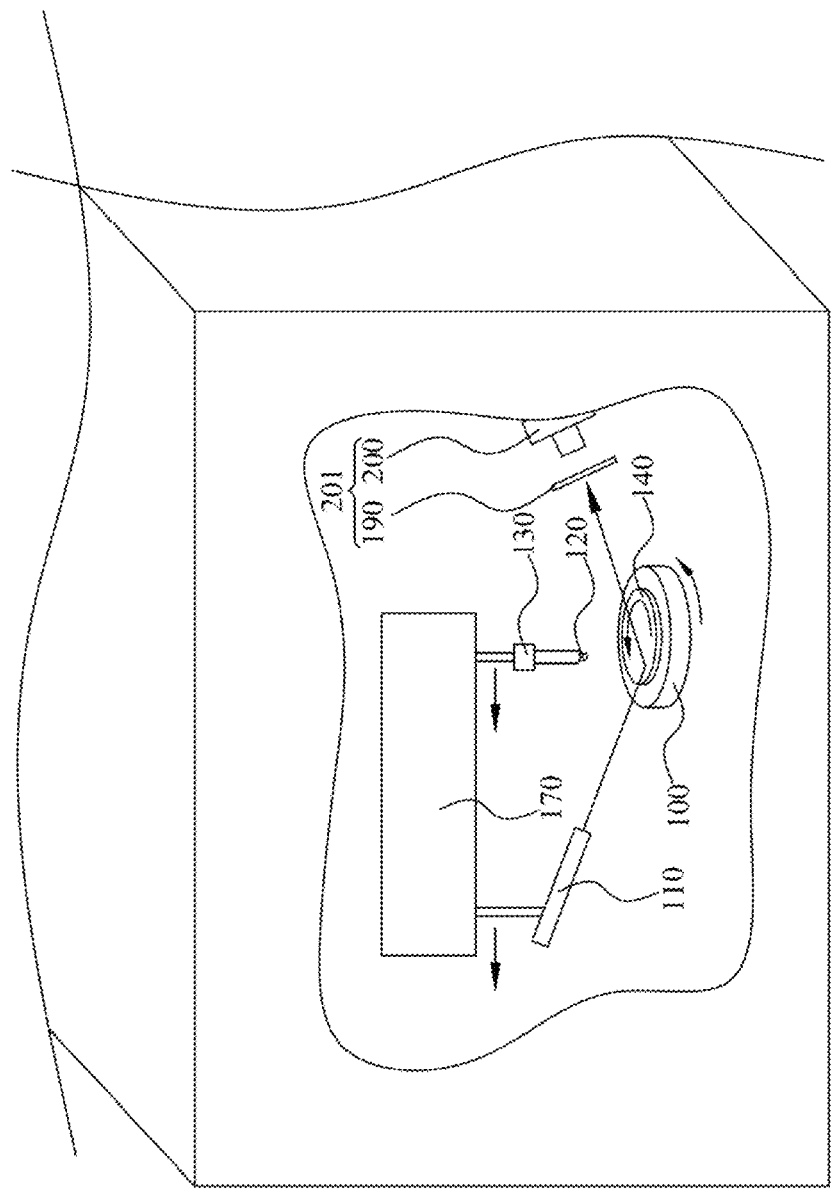
FIG. 8 is a second schematic view of an embodiment of an inspection system according to the present invention.

With reference to FIG. 8, the platform 100 can revolve and cause the silicon wafer 140 to rotate correspondingly, and the laser beam 111 accordingly irradiates on the surface of the silicon wafer 140 in a circular way. Furthermore, the present embodiment can further include a driving module 170 connected to the laser focus module 110 and the image pick-up module 130 to drive the laser focus module 110 and the image pick-up module 130 to move simultaneously, and to cause the laser beam 111 to irradiate on the surface of the silicon wafer 140 in a straight way. And combining the driving module 170 and the rotation of the platform 100, the laser beam 111 can irradiate on the surface of the silicon wafer thoroughly. After the inspection system 10 scans the whole surface of silicon wafer 140, the storage device 160 in FIG. 2 can build a data base about all the defects' sizes and positions.

Figure 9:
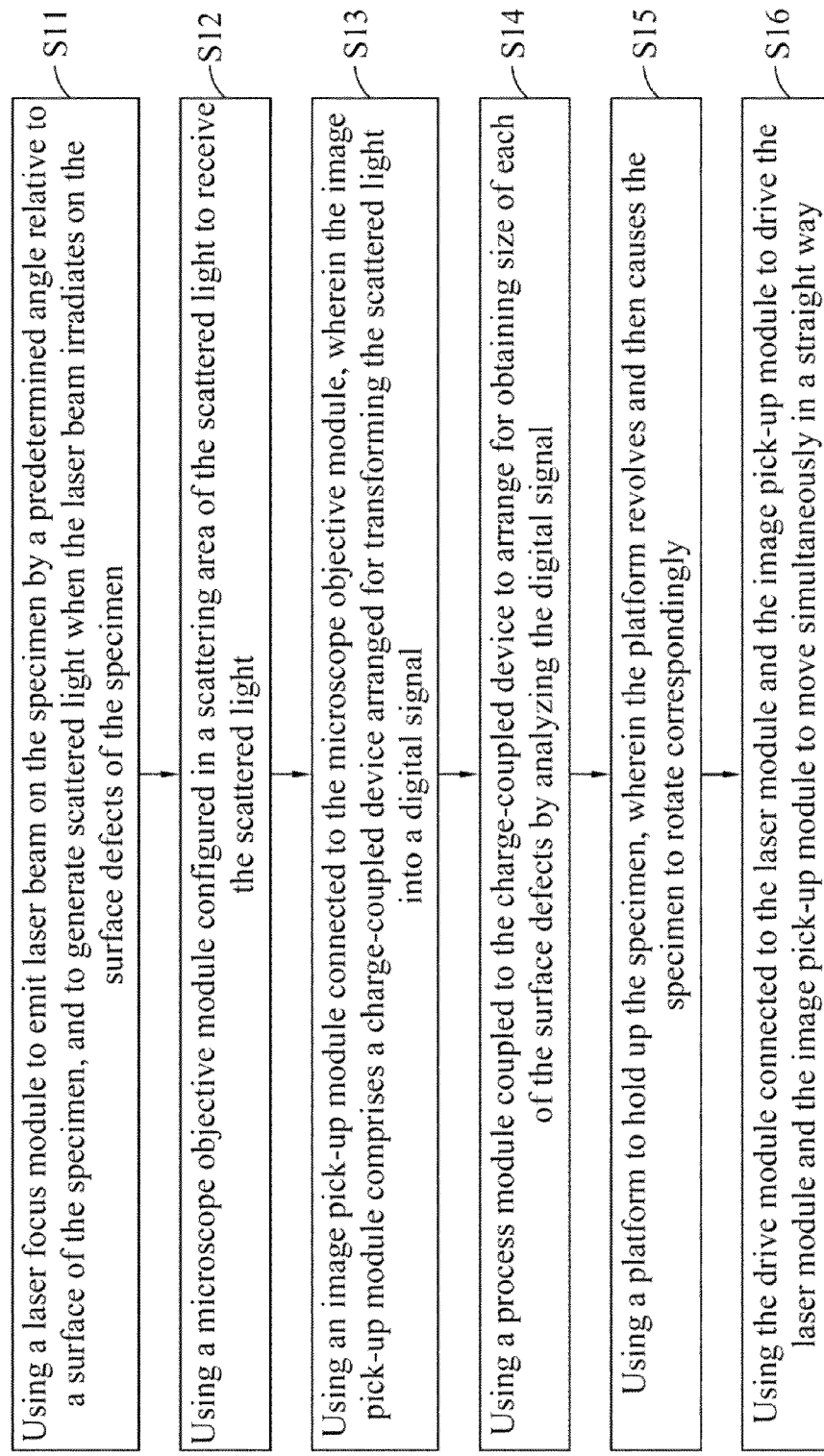
FIG. 9 is a flow process of an embodiment of an inspection method according to the present invention.

With reference to FIG. 9, the steps of inspection method for inspecting surface defects of a specimen according to an embodiment will be described below, and because the inspection system is described as above, some detail description of the inspection method will be neglected.

The inspection method for inspecting surface defects of a specimen includes the following steps:

S11: using a laser focus module to emit laser beam on the specimen by a predetermined angle relative to a surface of the specimen, and to generate scattered light when the laser beam irradiates on the surface defects of the specimen, wherein the predetermined angle can range from approximately 15° to approximately 40°. In some preferred embodiments, the predetermined angle can range from approximately 20° to approximately 30°.

S12: using a microscope objective module configured in a scattering area of the scattered light to receive the scattered light, and the laser focus module includes a laser source, a beam expander and a focusing lens set, and the beam expander is configured between the laser source and the focusing lens set. In present embodiment, the laser beam is a green light laser, but is not limited thereto.

S13: using an image pick-up module connected to the microscope objective module, wherein the image pick-up module includes a charge-coupled device arranged for transforming the scattered light into a digital signal.

S14: using a process module coupled to the charge-coupled device to arrange for obtaining sizes of the surface defects by analyzing the digital signal, wherein the process module can analyze the intensity of the scattered light to calculate the size of each of the surface defects.

S15: using a platform to hold up the specimen, wherein the platform revolves and then causes the specimen to rotate correspondingly, and the laser beam accordingly irradiates on the surface of the specimen in a circular way.

S16: using the drive module connected to the laser module and the image pick-up module to drive the laser module and the image pick-up module to move simultaneously, and causes the laser beam to irradiate on the surface of the specimen in a straight way.

During the step S13, in some embodiments further include using a reflected light capture module to capture a reflected light image, and using the process module to calculate the size of each of the surface defects by analyzing diameters of caustic curves from the reflected light image.

In summary, the present invention can evaluate the number and real sizes of the defects on the surface of the specimen by analyzing the intensity of scattered light or the diameter of the caustic curves obtained from the reflected light image. Therefore, the present invention can decrease the cost and increase the inspection speed without using the expensive high resolution image sensor and the high magnification object lens.

While the means of specific embodiments in present invention has been described by reference drawings, numerous modifications and variations could be made thereto by those skilled in the art without departing from the scope and spirit of the invention set forth in the claims. The modifications and variations should in a range limited by the specification of the present invention.

What is claimed is:

1. An inspection system for inspecting surface defects of a specimen, the system comprising:
    a laser focus module configured to emit laser beam on the specimen by a predetermined angle relative to a surface of the specimen, and to generate scattered light when the laser beam irradiates on the surface defects of the specimen;
    a microscope objective module configured in a scattering area of the scattered light to receive the scattered light;
    an image pick-up module comprising a charge-coupled device connected to the microscope objective module and arranged for transforming the scattered light into a digital signal;
    a process module coupled to the charge-coupled device and arranged for calculating sizes of the surface defects by analyzing the digital signal; and
    a reflected light capture module to capture a reflected light image, and the process module selectively calculates the size of each of the surface defects by analyzing diameters of caustic curves from the reflected light image.

2. The inspection system of claim 1, wherein the predetermined angle ranges from approximately 15° to approximately 40°.

3. The inspection system of claim 2, wherein the predetermined angle ranges from approximately 20° to approximately 30°.

4. The inspection system of claim 1, wherein the process module calculates the size of each of the surface defects by analyzing intensity of the scattered light according to the digital signal.

5. The inspection system of claim 1, wherein the laser focus module comprises a laser source, a beam expander and a focusing lens set, and the beam expander is configured between the laser source and the focusing lens set.

6. The inspection system of claim 1, wherein the laser beam is a green light laser.

7. The inspection system of claim 1, further comprises a platform held up the specimen to revolve and cause the specimen to rotate correspondingly, and the laser beam accordingly irradiates on the surface of the specimen in a circular way.

8. The inspection system of claim 7, further comprising a driving module which is connected to the laser focus module and the image pick-up module to drive the laser focus module and the image pick-up module to move simultaneously, and to cause the laser beam to irradiate on the surface of the specimen in a straight way.

9. A inspection method for inspecting surface defects of a specimen, the method comprising:

using a laser focus module to emit laser beam on the specimen by a predetermined angle relative to a surface of the specimen, and to generate scattered light when the laser beam irradiates on the surface defects of the specimen;

using a microscope objective module configured in a scattering area of the scattered light to receive the scattered light;

using an image pick-up module connected to the microscope objective module, wherein the image pick-up module comprises a charge-coupled device arranged for transforming the scattered light into a digital signal;

using a process module coupled to the charge-coupled device to arrange for obtaining sizes of the surface defects by analyzing the digital signal; and using the reflected light capture module to capture a reflected light image, and using the process module to calculate the size of each of the surface defects by analyzing diameters of caustic curves from the reflected light image.

10. The inspection method of claim 9, wherein the predetermined angle ranges from approximately 15° to approximately 40°.

11. The inspection method of claim 10, wherein the predetermined angle ranges from approximately 20° to approximately 30°.

12. The inspection method of claim 9, wherein the step of using the process module further comprises using the process module to analyze intensity of the scattered light according to the digital signal to calculate the size of each of the surface defects.

13. The inspection method of claim 9, wherein the laser focus module comprises a laser source, a beam expander and a focusing lens set, and the beam expander is configured between the laser source and the focusing lens set.

14. The inspection method of claim 9, wherein the laser beam is a green light laser.

15. The inspection method of claim 9, further comprises using the platform to hold up the specimen, wherein the platform revolves and then causes the specimen to rotate correspondingly, and the laser beam accordingly irradiates on the surface of the specimen in a circular way.

16. The inspection method of claim 15, wherein the step of using the platform further comprises using a drive module connected to the laser module and the image pick-up module to drive the laser module and the image pick-up module to move simultaneously, and causes the laser beam to irradiate on the surface of the specimen in a straight way.

* * * * *